United States Patent
Harari et al.

(10) Patent No.: US 11,065,122 B2
(45) Date of Patent: Jul. 20, 2021

(54) TECHNIQUES FOR USE WITH PROSTHETIC VALVE LEAFLETS

(71) Applicant: CARDIOVALVE LTD., Or Yehuda (IL)

(72) Inventors: Boaz Harari, Ganey Tikva (IL); Ilia Hariton, Zichron Yaakov (IL)

(73) Assignee: CARDIOVALVE LTD., Or Yehuda (IL)

( * ) Notice: Subject to any disclaimer, the term of this patent is extended or adjusted under 35 U.S.C. 154(b) by 0 days.

(21) Appl. No.: 16/756,235

(22) PCT Filed: Jan. 8, 2018

(86) PCT No.: PCT/IL2018/050024
§ 371 (c)(1),
(2) Date: Apr. 15, 2020

(87) PCT Pub. No.: WO2019/077595
PCT Pub. Date: Apr. 25, 2019

(65) Prior Publication Data
US 2020/0281723 A1    Sep. 10, 2020

Related U.S. Application Data

(63) Continuation of application No. 15/788,407, filed on Oct. 19, 2017, now Pat. No. 9,895,226.

(51) Int. Cl.
*A61F 2/24* (2006.01)
*G01N 3/04* (2006.01)
(Continued)

(52) U.S. Cl.
CPC .............. *A61F 2/2472* (2013.01); *G01L 1/24* (2013.01); *G01N 3/04* (2013.01);
(Continued)

(58) Field of Classification Search
CPC . A61F 2/2472; A61F 2002/7635; G01N 3/04; G01B 11/02; G01B 11/14; G01L 1/24; H04N 7/18
See application file for complete search history.

(56) References Cited

U.S. PATENT DOCUMENTS 4,972,494 A    11/1990  White et al.
5,713,948 A    2/1998   Uflacker
(Continued)

FOREIGN PATENT DOCUMENTS

CN    103974674    8/2014
EP    0170262      2/1986
(Continued)

OTHER PUBLICATIONS

International Search Report and Written Opinion issued in PCT Application No. PCT/IL2018/050024 dated Jun. 20, 2018.
(Continued)

*Primary Examiner* — Jonathan M Dunlap
(74) *Attorney, Agent, or Firm* — Dilworth IP, LLC

(57) ABSTRACT

A prosthetic valve leaflet is placed across a bar, and the bar is positioned such that the leaflet drapes over the bar and blocks a beam of light emitted by a light source. While the leaflet remains draped over the bar, the bar is elevated at least until the leaflet stops blocking the beam. An elevation of the bar from the beam at which the leaflet stopped blocking the beam is identified. Other embodiments are also described.

16 Claims, 7 Drawing Sheets

(51) Int. Cl.
 *G01L 1/24* (2006.01)
 *G01B 11/02* (2006.01)
 *H04N 7/18* (2006.01)
 *A61F 2/76* (2006.01)
 *G01B 11/14* (2006.01)

(52) U.S. Cl.
 CPC ....... *A61F 2002/7635* (2013.01); *G01B 11/02* (2013.01); *G01B 11/14* (2013.01); *H04N 7/18* (2013.01)

(56) References Cited

U.S. PATENT DOCUMENTS

| | | |
|---|---|---|
| 5,776,140 A | 7/1998 | Cottone |
| 5,957,949 A | 9/1999 | Leonhardt et al. |
| 5,961,549 A * | 10/1999 | Nguyen ............... A61F 2/2412 623/2.12 |
| 6,010,530 A | 1/2000 | Goicoechea |
| 6,245,105 B1 | 6/2001 | Nguyen et al. |
| 6,402,780 B2 | 6/2002 | Williamson, IV et al. |
| 6,413,275 B1 | 7/2002 | Nguyen et al. |
| 6,454,799 B1 | 9/2002 | Schreck |
| 6,837,902 B2 | 1/2005 | Nguyen et al. |
| 7,018,406 B2 | 3/2006 | Seguin et al. |
| 7,585,321 B2 | 9/2009 | Cribier |
| 8,361,144 B2 | 1/2013 | Fish et al. |
| 8,568,475 B2 | 10/2013 | Nguyen et al. |
| 8,628,571 B1 | 1/2014 | Hacohen et al. |
| 8,728,155 B2 | 5/2014 | Montorfano et al. |
| 8,850,898 B2 | 10/2014 | Johnsen |
| 8,852,272 B2 | 10/2014 | Gross et al. |
| 8,870,948 B1 | 10/2014 | Erzberger et al. |
| 8,870,950 B2 | 10/2014 | Hacohen |
| 8,998,982 B2 | 4/2015 | Richter et al. |
| 9,017,399 B2 | 4/2015 | Gross et al. |
| 9,023,100 B2 | 5/2015 | Quadri et al. |
| 9,095,434 B2 | 8/2015 | Rowe |
| 9,097,620 B2 | 8/2015 | Caron et al. |
| 9,180,009 B2 | 11/2015 | Majkrzak et al. |
| 9,232,995 B2 | 1/2016 | Kovalsky et al. |
| 9,241,791 B2 | 1/2016 | Braido et al. |
| 9,241,792 B2 | 1/2016 | Benichou et al. |
| 9,248,014 B2 | 2/2016 | Lane et al. |
| 9,358,107 B2 * | 6/2016 | Nguyen ................. A61F 2/24 |
| 9,387,078 B2 | 7/2016 | Gross et al. |
| 9,439,757 B2 | 9/2016 | Wallace et al. |
| 9,492,273 B2 | 11/2016 | Wallace et al. |
| 9,554,899 B2 | 1/2017 | Granada et al. |
| 9,561,103 B2 | 2/2017 | Granada et al. |
| 9,662,203 B2 | 5/2017 | Sheahan et al. |
| 9,681,952 B2 | 6/2017 | Hacohen et al. |
| 9,763,657 B2 | 9/2017 | Hacohen et al. |
| D800,908 S | 10/2017 | Hariton et al. |
| 9,788,941 B2 | 10/2017 | Hacohen |
| 9,895,226 B1 | 2/2018 | Harari et al. |
| 9,987,132 B1 | 6/2018 | Hariton et al. |
| 10,010,414 B2 | 7/2018 | Cooper et al. |
| 10,143,552 B2 | 12/2018 | Wallace et al. |
| 10,149,761 B2 | 12/2018 | Granada et al. |
| 10,154,906 B2 | 12/2018 | Granada et al. |
| 10,182,908 B2 | 1/2019 | Tubishevitz et al. |
| 10,226,341 B2 | 3/2019 | Gross et al. |
| 10,245,143 B2 | 4/2019 | Gross et al. |
| 10,258,471 B2 | 4/2019 | Lutter et al. |
| 10,321,995 B1 | 6/2019 | Christianson et al. |
| 10,327,895 B2 | 6/2019 | Lozonschi et al. |
| 10,376,361 B2 | 8/2019 | Gross et al. |
| 10,531,866 B2 | 1/2020 | Hariton et al. |
| 10,531,872 B2 | 1/2020 | Hacohen et al. |
| 10,548,731 B2 | 2/2020 | Lashinski et al. |
| 10,575,948 B2 | 3/2020 | Iamberger et al. |
| 2002/0032481 A1 | 3/2002 | Gabbay et al. |
| 2002/0151970 A1 | 10/2002 | Garrison et al. |
| 2003/0074059 A1 * | 4/2003 | Nguyen ............... A61F 2/2472 623/2.13 |
| 2004/0186558 A1 | 9/2004 | Pavcnik et al. |
| 2004/0249433 A1 | 12/2004 | Freitag |
| 2005/0137690 A1 | 6/2005 | Salahieh et al. |
| 2005/0240200 A1 | 10/2005 | Bergheim |
| 2005/0251251 A1 | 11/2005 | Cribier |
| 2006/0004469 A1 | 1/2006 | Sokel |
| 2006/0020327 A1 | 1/2006 | Lashinski et al. |
| 2006/0052867 A1 | 3/2006 | Revuelta et al. |
| 2006/0195183 A1 | 8/2006 | Navia et al. |
| 2006/0259137 A1 | 11/2006 | Artof et al. |
| 2006/0282150 A1 | 12/2006 | Olson et al. |
| 2007/0056346 A1 | 3/2007 | Spenser et al. |
| 2007/0198077 A1 | 8/2007 | Cully et al. |
| 2007/0213810 A1 | 9/2007 | Newhauser et al. |
| 2007/0219630 A1 | 9/2007 | Chu |
| 2008/0071361 A1 | 3/2008 | Tuval et al. |
| 2008/0147182 A1 | 6/2008 | Righini et al. |
| 2008/0200980 A1 | 8/2008 | Robin et al. |
| 2008/0234814 A1 | 9/2008 | Salahieh et al. |
| 2008/0281411 A1 | 11/2008 | Berreklouw |
| 2009/0005863 A1 | 1/2009 | Goetz et al. |
| 2009/0125098 A1 | 5/2009 | Chuter |
| 2009/0157175 A1 | 6/2009 | Benichou |
| 2009/0259306 A1 | 10/2009 | Rowe |
| 2010/0023120 A1 | 1/2010 | Holecek et al. |
| 2010/0100167 A1 | 4/2010 | Bortlein et al. |
| 2010/0161036 A1 | 6/2010 | Pintor et al. |
| 2010/0331971 A1 | 12/2010 | Keränen et al. |
| 2011/0004299 A1 | 1/2011 | Navia et al. |
| 2011/0021985 A1 | 1/2011 | Spargias |
| 2011/0029072 A1 | 2/2011 | Gabbay |
| 2011/0112632 A1 | 5/2011 | Chau et al. |
| 2011/0137397 A1 | 6/2011 | Chau et al. |
| 2011/0144742 A1 | 6/2011 | Madrid et al. |
| 2011/0208283 A1 | 8/2011 | Rust |
| 2011/0208298 A1 | 8/2011 | Tuval et al. |
| 2011/0218620 A1 | 9/2011 | Meiri et al. |
| 2011/0224785 A1 | 9/2011 | Hacohen |
| 2011/0282439 A1 | 11/2011 | Thill et al. |
| 2011/0307049 A1 | 12/2011 | Kao |
| 2011/0319989 A1 | 12/2011 | Lane et al. |
| 2012/0016468 A1 | 1/2012 | Robin et al. |
| 2012/0022629 A1 | 1/2012 | Perera et al. |
| 2012/0022639 A1 | 1/2012 | Hacohen et al. |
| 2012/0022640 A1 | 1/2012 | Gross et al. |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0089223 A1 | 4/2012 | Nguyen et al. |
| 2012/0300063 A1 | 11/2012 | Majkrzak et al. |
| 2012/0310328 A1 | 12/2012 | Olson et al. |
| 2013/0018458 A1 | 1/2013 | Yohanan et al. |
| 2013/0035759 A1 | 2/2013 | Gross et al. |
| 2013/0150956 A1 | 6/2013 | Yohanan et al. |
| 2013/0261738 A1 | 10/2013 | Clague et al. |
| 2013/0304200 A1 | 11/2013 | Mclean et al. |
| 2014/0000112 A1 | 1/2014 | Braido et al. |
| 2014/0005778 A1 | 1/2014 | Buchbinder et al. |
| 2014/0018915 A1 | 1/2014 | Biadillah et al. |
| 2014/0142688 A1 | 5/2014 | Duffy et al. |
| 2014/0172077 A1 | 6/2014 | Bruchman et al. |
| 2014/0207231 A1 | 7/2014 | Hacohen et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0257467 A1 | 9/2014 | Lane et al. |
| 2014/0277409 A1 | 9/2014 | Börtlein et al. |
| 2014/0277411 A1 | 9/2014 | Börtlein et al. |
| 2014/0277418 A1 | 9/2014 | Miller |
| 2014/0358224 A1 | 12/2014 | Tegels et al. |
| 2015/0142100 A1 | 5/2015 | Morriss et al. |
| 2015/0157458 A1 | 6/2015 | Thambar et al. |
| 2015/0173896 A1 | 6/2015 | Richter et al. |
| 2015/0173897 A1 | 6/2015 | Raanani et al. |
| 2015/0272734 A1 | 10/2015 | Sheps et al. |
| 2015/0320556 A1 | 11/2015 | Levi et al. |
| 2015/0327994 A1 | 11/2015 | Morriss et al. |
| 2015/0351903 A1 | 12/2015 | Morriss et al. |
| 2015/0351904 A1 | 12/2015 | Cooper et al. |

(56) References Cited

U.S. PATENT DOCUMENTS

| | | |
|---|---|---|
| 2016/0030169 A1 | 2/2016 | Shahriari |
| 2016/0317305 A1 | 11/2016 | Pelled et al. |
| 2016/0324635 A1 | 11/2016 | Vidlund et al. |
| 2016/0374801 A1 | 12/2016 | Jimenez et al. |
| 2016/0374802 A1 | 12/2016 | Levi et al. |
| 2017/0056166 A1 | 3/2017 | Ratz et al. |
| 2017/0135816 A1 | 5/2017 | Lashinski et al. |
| 2017/0189174 A1 | 7/2017 | Braido et al. |
| 2017/0333187 A1 | 11/2017 | Hariton et al. |
| 2018/0000580 A1 | 1/2018 | Wallace et al. |
| 2018/0021129 A1 | 1/2018 | Peterson et al. |
| 2018/0125644 A1 | 5/2018 | Conklin |
| 2018/0153687 A1 | 6/2018 | Hariton et al. |
| 2018/0206983 A1 | 7/2018 | Noe et al. |
| 2018/0250126 A1 | 9/2018 | O'Connor et al. |
| 2018/0296336 A1 | 10/2018 | Cooper et al. |
| 2018/0344457 A1 | 12/2018 | Gross et al. |
| 2018/0353294 A1 | 12/2018 | Calomeni et al. |
| 2019/0053896 A1 | 2/2019 | Adamek-Bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0105153 A1 | 4/2019 | Barash et al. |
| 2019/0117391 A1 | 4/2019 | Humair |
| 2019/0167423 A1 | 6/2019 | Hariton et al. |
| 2019/0175339 A1 | 6/2019 | Vidlund |
| 2019/0183639 A1 | 6/2019 | Moore |
| 2019/0216602 A1 | 7/2019 | Lozonschi |
| 2019/0350701 A1 | 11/2019 | Adamek-Bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2020/0000579 A1 | 1/2020 | Manash et al. |
| 2020/0015964 A1 | 1/2020 | Noe et al. |
| 2020/0060818 A1 | 2/2020 | Geist et al. |
| 2020/0085578 A1 | 3/2020 | Kislev et al. |

FOREIGN PATENT DOCUMENTS

| | | |
|---|---|---|
| EP | 1264582 | 12/2002 |
| JP | S53152790 | 12/1978 |
| KR | 20010046894 | 6/2001 |
| WO | 9843557 A1 | 10/1998 |
| WO | 01/82832 | 11/2001 |
| WO | 2010/006627 | 1/2010 |
| WO | 2010/057262 | 5/2010 |
| WO | 2012/048035 | 4/2012 |
| WO | 2013/021374 | 2/2013 |
| WO | 2013/021375 | 2/2013 |
| WO | 2013/059747 | 4/2013 |
| WO | 2013/072496 | 5/2013 |
| WO | 2013/078497 | 6/2013 |
| WO | 2013/175468 | 11/2013 |
| WO | 2014/076696 | 5/2014 |
| WO | 2014/115149 | 7/2014 |
| WO | 2014/164364 | 10/2014 |
| WO | 2016/016899 | 2/2016 |
| WO | 2016/125160 | 8/2016 |
| WO | 2018/025263 | 2/2018 |
| WO | 2018/029680 | 2/2018 |
| WO | 2018/039631 | 3/2018 |
| WO | 2019/026059 | 2/2019 |
| WO | 2019/030753 | 2/2019 |
| WO | 2019/077595 | 4/2019 |
| WO | 2019/116369 | 6/2019 |
| WO | 2019/138400 | 7/2019 |
| WO | 2019/195860 | 10/2019 |
| WO | 2019/202579 | 10/2019 |
| WO | 2020/058972 | 3/2020 |

OTHER PUBLICATIONS

Notice of Allowance dated Dec. 22, 2017, which issued during the prosecution of U.S. Appl. No. 15/788,407.

An International Search Report and a Written Opinion both dated Jun. 20, 2018, which issued during the prosecution of Applicant's PCT/IL2018/050024.

An International Preliminary Report on Patentability dated Apr. 21, 2020, which issued during the prosecution of Applicant's PCT/IL2018/050024.

An International Search Report and a Written Opinion both dated Nov. 9, 2018, which issued during the prosecution of Applicant's PCT/IL2018/050869.

An International Search Report and a Written Opinion both dated May 13, 2019, which issued during the prosecution of Applicant's PCT/IL2018/051350.

An International Search Report and a Written Opinion both dated Apr. 25, 2019, which issued during the prosecution of Applicant's PCT/IL2019/050142.

An International Search Report and a Written Opinion both dated Jan. 25, 2019, which issued during the prosecution of Applicant's PCT/IL2018/051122.

An International Search Report and a Written Opinion both dated Dec. 5, 2018, which issued during the prosecution of Applicant's PCT/IL2018/050725.

An International Preliminary Report on Patentability dated Feb. 12, 2019, which issued during the prosecution of Applicant's PCT/IL2017/050873.

An International Preliminary Report on Patentability dated Feb. 5, 2019, which issued during the prosecution of Applicant's PCT/IL2017/050849.

An Office Action dated Mar. 25, 2019, which issued during the prosecution of European Patent Application No. 14710060.6.

An Office Action dated Oct. 25, 2018, which issued during the prosecution of U.S. Appl. No. 14/763,004.

An Office Action dated Mar. 4, 2019, which issued during the prosecution of U.S. Appl. No. 14/763,004.

An Office Action dated Jan. 9, 2019, which issued during the prosecution of U.S. Appl. No. 15/329,920.

An Office Action dated Jan. 30, 2019, which issued during the prosecution of U.S. Appl. No. 15/872,501.

An Office Action dated May 14, 2020, which issued during the prosecution of U.S. Appl. No. 16/132,937.

An Office Action dated Feb. 5, 2019, which issued during the prosecution of U.S. Appl. No. 15/899,858.

An Office Action dated May 23, 2019, which issued during the prosecution of U.S. Appl. No. 15/668,659.

An Office Action dated May 1, 2019, which issued during the prosecution of U.S. Appl. No. 15/691,032.

An Office Action dated May 16, 2019, which issued during the prosecution of U.S. Appl. No. 15/433,547.

An Office Action dated Aug. 1, 2019, which issued during the prosecution of U.S. Appl. No. 15/668,559.

An Office Action dated Jun. 25, 2019, which issued during the prosecution of U.S. Appl. No. 15/329,920.

An Office Action dated Nov. 1, 2019, which issued during the prosecution of U.S. Appl. No. 15/872,501.

An Office Action dated Aug. 16, 2019, which issued during the prosecution of U.S. Appl. No. 15/668,659.

An Office Action dated Jun. 19, 2019, which issued during the prosecution of U.S. Appl. No. 15/682,789.

An Office Action dated Jun. 14, 2019, which issued during the prosecution of U.S. Appl. No. 15/703,385.

An Office Action dated Oct. 4, 2019, which issued during the prosecution of U.S. Appl. No. 16/183,140.

An Office Action dated Sep. 13, 2019, which issued during the prosecution of U.S. Appl. No. 16/460,313.

An Office Action dated Nov. 26, 2019, which issued during the prosecution of U.S. Appl. No. 16/532,945.

An Office Action dated Jun. 13, 2019, which issued during the prosecution of U.S. Appl. No. 16/388,038.

Sündermann, Simon H., et al. "Feasibility of the Engager™ aortic transcatheter valve system using a flexible over-the-wire design." European Journal of Cardio-Thoracic Surgery 42.4 (2012): e48-e52.

Serruys, P. W., Piazza, N., Cribier, A., Webb, J., Laborde, J. C., & de Jaegere, P. (Eds.). (2009). Transcatheter aortic valve implanta-

(56) References Cited

OTHER PUBLICATIONS tion: tips and tricks to avoid failure. CRC Press.—Screenshots from Google Books downloaded from: https://books.google.co.il/books?id=FLzLBQAAQBAJ&lpg=PA198&ots=soqWrDH-y_&dq=%20%22Edwards%20SAPIEN%22&lr&pg=PA20#v=onepage&q=%22Edwards%20SAPlEN%22&f=false ; Downloaded on Jun. 18, 2020.

Notice of Allowance dated May 7, 2020, which issued during the prosecution of U.S. Appl. No. 16/637,166.

An Office Action dated Aug. 7, 2020, which issued during the prosecution of U.S. Appl. No. 15/668,659.

Notice of Allowance dated Jul. 29, 2020, which issued during the prosecution of U.S. Appl. No. 16/132,937.

Notice of Allowance dated Sep. 10, 2020, which issued during the prosecution of U.S. Appl. No. 15/600,190.

An Office Action dated Jul. 29, 2020, which issued during the prosecution of U.S. Appl. No. 16/269,328.

Notice of Allowance dated Aug. 26, 2020, which issued during the prosecution of U.S. Appl. No. 16/269,328.

An Office Action dated Jul. 14, 2020, which issued during the prosecution of U.S. Appl. No. 16/324,339.

Notice of Allowance dated Aug. 28, 2020, which issued during the prosecution of U.S. Appl. No. 16/324,339.

An Office Action summarized English translation and Search Report dated Jul. 3, 2020, which issued during the prosecution of Chinese Patent Application No. 201780061210.3.

Tchetche, D. and Nicolas M. Van Mieghem: "New-generation TAVI devices: description and specifications" EuroIntervention, 2014, No. 10:U90-U100.

An International Search Report and a Written Opinion both dated Jun. 24, 2020, which issued during the prosecution of Applicant's PCT/IL2019/051398.

Symetis S.A.: "ACURATE neo™ Aortic Bioprosthesis for Implantation using the ACURATE neo™ TA Transapical Delivery System in Patients with Severe Aortic Stenosis," Clinical Investigation Plan, Protocol No. 2015-01, Vs. No. 2, 2015:1-76.

An Office Action dated Jan. 6, 2020, which issued during the prosecution of U.S. Appl. No. 16/660,231.

An Office Action dated Dec. 31, 2019, which issued during the prosecution of U.S. Appl. No. 16/183,140.

An Office Action dated Jan. 14, 2020, which issued during the prosecution of U.S. Appl. No. 16/284,331.

Notice of Allowance dated Jan. 13, 2020, which issued during the prosecution of U.S. Appl. No. 15/956,956.

European Search Report dated Mar. 5, 2020 which issued during the prosecution of Applicant's European App No. 17752184.6.

European Search Report dated Mar. 4, 2020 which issued during the prosecution of Applicant's European App No. 16706913.7.

Notice of Allowance dated Mar. 12, 2020, which issued during the prosecution of U.S. Appl. No. 16/460,313.

An Office Action dated Jan. 9, 2020, which issued during the prosecution of U.S. Appl. No. 15/600,190.

An Office Action dated Jan. 3, 2020, which issued during the prosecution of U.S. Appl. No. 16/678,355.

An Office Action dated Feb. 6, 2020, which issued during the prosecution of U.S. Appl. No. 15/668,659.

An International Preliminary Report on Patentability dated Oct. 20, 2020, which issued during the prosecution of Applicant's PCT/IL2019/050142.

An Office Action dated Oct. 5, 2020, which issued during the prosecution of Canadian Patent Application No. 2,973,940.

Notice of Allowance dated Nov. 19, 2020, which issued during the prosecution of U.S. Appl. No. 16/318,025.

An Office Action dated Sep. 24, 2020, which issued during the prosecution of U.S. Appl. No. 16/811,732.

An Office Action summarized English translation and Search Report dated Nov. 25, 2020, which issued during the prosecution of Chinese Patent Application No. 201910449820.1.

An Office Action dated Nov. 30, 2020, which issued during the prosecution of U.S. Appl. No. 16/138,129.

Notice of Allowance dated Oct. 19, 2020, which issued during the prosecution of U.S. Appl. No. 16/937,216.

* cited by examiner

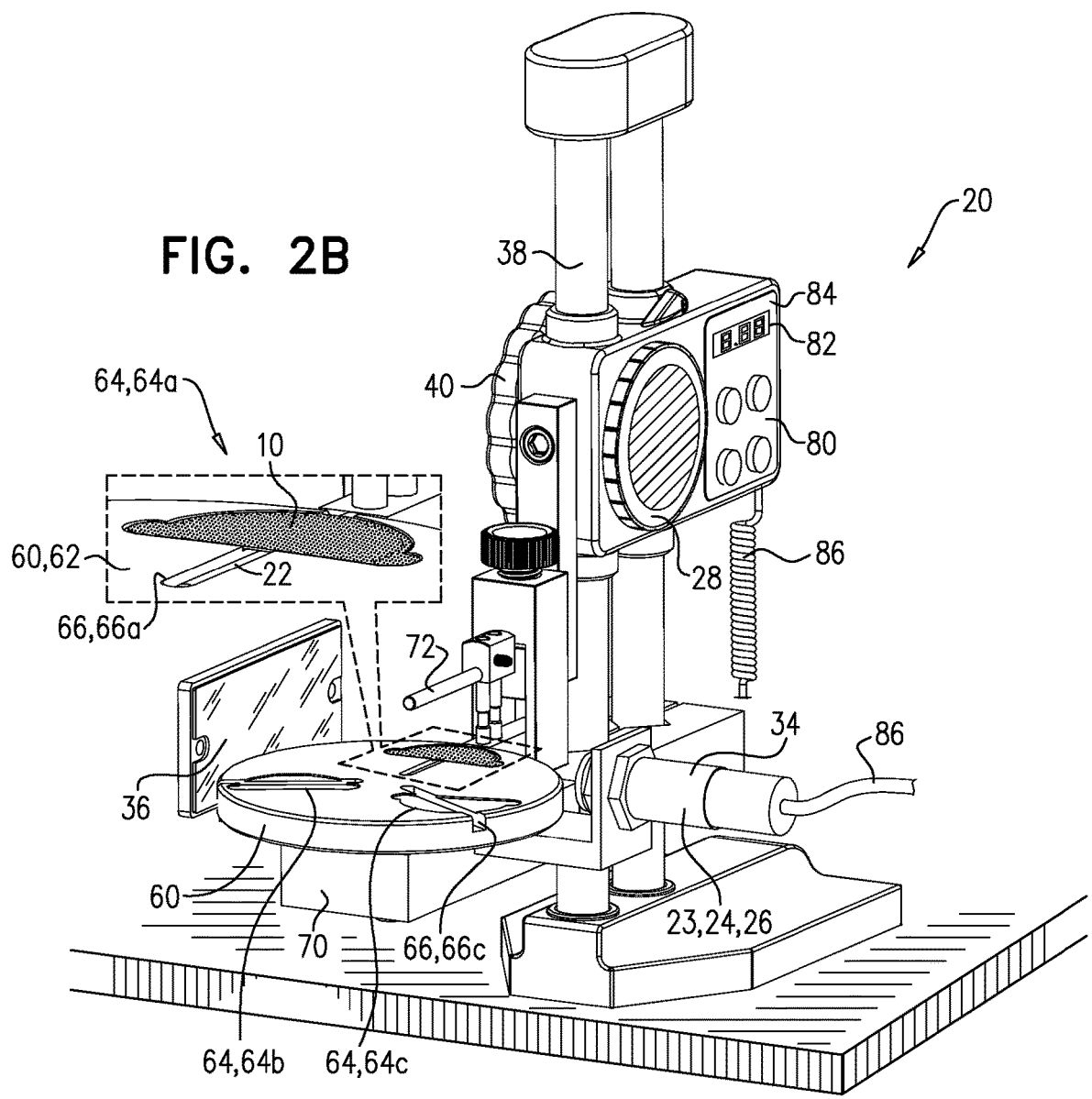

US 11,065,122 B2

TECHNIQUES FOR USE WITH PROSTHETIC VALVE LEAFLETS

CROSS-REFERENCES TO RELATED APPLICATIONS

The present application is the US National Phase of PCT application IL2018/050024 to Harari et al., filed Jan. 8, 2018, and entitled "Techniques for use with prosthetic valve leaflets," which published as WO 2019/077595, and which is a Continuation of U.S. patent application Ser. No. 15/788,407 to Harari et al., filed Oct. 19, 2017, and entitled "Techniques for use with prosthetic valve leaflets" (now U.S. Pat. No. 9,895,226).

FIELD OF THE INVENTION

Some applications of the present invention relate in general to prosthetic heart valves. More specifically, some applications of the present invention relate to techniques for testing the flexibility of prosthetic leaflets to be used in prosthetic heart valves.

BACKGROUND

Prosthetic heart valves may be constructed of a frame to which prosthetic leaflets are attached, the leaflets providing check-valve functionality by opening in response to blood flow in a first direction, and closing in response to blood flow in a second direction. In order to inhibit leakage ("regurgitation") of blood between the closed leaflets in the second direction, it is important that the leaflets coapt well against each other.

SUMMARY OF THE INVENTION

Techniques are provided for determining one or more flexibility values of a prosthetic valve leaflet by draping the leaflet over a bar in one or more orientations, and measuring how low the leaflet hangs below the bar. This measurement is made by elevating the bar and measuring an elevation of the bar with respect to a reference. For some applications, the bar is positioned such that the leaflet draped over the bar blocks a light beam, and the bar is then elevated until the leaflet no longer blocks the light beam. The flexibility value is determined responsively to the elevation of the bar at which the leaflet no longer blocks the light beam.

Prosthetic valves are constructed using prosthetic valve leaflets that have complementary flexibility values.

There is therefore provided, in accordance with an application of the present invention, apparatus for testing a prosthetic heart valve leaflet, the apparatus including:

a vertical post, having a longitudinal axis;

a horizontal bar having a bar-axis that lies on a vertical bar-plane, the bar being configured to support the leaflet along the bar-axis such that the leaflet drapes over the bar;

a linear actuator, movably coupling the bar to the post, actuation of the actuator moving the bar vertically in the bar-plane;

a light source, configured to emit a beam of light, and oriented to direct the beam through the bar-plane;

a gauge, configured to measure an elevation of the bar above the beam; and a detector, configured and positioned to detect the beam, and to generate a detection-signal indicative of detection of the beam.

In an application, the bar extends laterally away from the post.

In an application, the light source is disposed laterally from the post.

In an application, the light source is oriented to direct the beam horizontally through the bar-plane.

In an application, the coupling, by the actuator, of the bar to the post, is such that the moving of the bar vertically in the bar-plane includes moving the bar vertically through the beam.

In an application, the light source includes a laser, and the light beam includes a laser beam.

In an application, the apparatus further includes a platform having a surface, the platform coupled to the post such that the bar-plane intersects the platform, the actuation of the actuator moving the bar vertically, in the bar-plane, with respect to the platform.

In an application, the light source is adjustably coupled to the platform, such that a distance between the beam of light and the surface is adjustable by adjusting a position of the light source with respect to the platform.

In an application, the bar has an initial position with respect to the platform, in which the leaflet is placeable across the bar and in contact with the surface.

In an application, in the initial position, the bar is disposed below the surface.

In an application, the platform has a guide that defines a guide-outline that (i) corresponds to a leaflet-outline of the leaflet, and (ii) has a guide-outline position and a guide-outline orientation that indicate, respectively, a leaflet-outline position and a leaflet-outline orientation in which the leaflet is to be placed when the leaflet is placed across the bar and in contact with the surface.

In an application, the platform is coupled to the post such that the bar-plane bisects the guide-outline.

In an application, the platform is coupled to the post such that the bar-plane bisects the guide-outline symmetrically.

In an application:

the platform is a first platform, the guide is a first guide, the guide-outline is a first guide-outline, the apparatus further includes a coupling, the first platform is removably couplable to the post via the coupling when the first platform is coupled to the post via the coupling, the bar-plane bisects the first guide-outline at a first angle, the apparatus further includes a second platform that has a second guide that defines a second guide-outline that corresponds to the leaflet-outline of the leaflet, the second platform is removably couplable to the post via the coupling, and when the second platform is coupled to the post via the coupling, the bar-plane bisects the second guide-outline at a second angle.

In an application:

the guide is a first guide, the guide-outline is a first guide-outline, the platform has a second guide that defines a second guide-outline that corresponds to the leaflet-outline of the leaflet, the apparatus has a first guide-state in which the bar-plane bisects the first guide-outline, the apparatus has a second guide-state in which the bar-plane bisects the second guide-outline, and the apparatus further includes a coupling via which the platform is movably coupled to the post, such that movement of the platform with respect to the post transitions the apparatus between the first guide-state and the second guide-state.

In an application, in the first guide-state, the bar-plane bisects the first guide-outline at a first angle, and in the second guide-state, the bar-plane bisects the second guide-outline at a second angle.

In an application, in the first guide-state, the bar-plane bisects the first guide-outline symmetrically, but in the second guide-state, the bar-plane bisects the second guide-outline asymmetrically.

In an application, the coupling is a rotating coupling, and rotation of the platform with respect to the post via the rotating coupling transitions the apparatus between the first guide-state and the second guide-state.

In an application, the platform defines a longitudinal hollow that lies on the bar-plane, and the bar, in its initial position, is disposed in the hollow.

In an application, the apparatus further includes a clamping element, movably coupled to the bar, and configured to clamp the leaflet to the bar.

In an application, the clamping element includes a rod, parallel to the bar, and configured to clamp the leaflet against the bar along the bar-axis.

In an application, the apparatus further includes a spring that provides a clamping force to clamping element.

There is further provided, in accordance with an application of the present invention, apparatus for testing a prosthetic heart valve leaflet, the apparatus including:

a bar having a bar-axis, the bar being configured to support the leaflet along the bar-axis such that the leaflet drapes over the bar;

a light source, configured to emit a beam of light;

a detector, configured to detect the beam, and to generate a detection-signal indicative of detection of the beam;

a linear actuator, movably coupling the bar to the light source, actuation of the actuator moving the bar with respect to the beam;

a gauge, configured to measure an elevation of the bar above the beam, the elevation changing with the moving of the bar by the actuator;

a display, and circuitry, electrically connected to the detector, the gauge, and the display, and configured:
  to receive, from the gauge, the measured elevation,
  to receive the detection-signal from the detector, and
  in response to the detection-signal, to drive the display to display the elevation that was measured when the detection-signal was received by the circuitry.

In an application, the linear actuator is configured such that the actuation of the actuator moves the bar through the beam.

In an application, the gauge is configured to continuously measure the elevation, and the circuitry is configured to continuously receive the measured elevation.

In an application, the circuitry is configured:
  while the detection-signal is not received by the circuitry, to continuously drive the display to display the continuously-measured elevation, and
  in response to the detection-signal, to maintain, on the display, the elevation that was measured at a time that the detection-signal was received by the circuitry.

There is further provided, in accordance with an application of the present invention, a method for determining a flexibility of a prosthetic heart valve leaflet, the method including:

placing the leaflet across a bar, and positioning the bar such that the leaflet drapes over the bar and blocks a beam of light emitted by a light source;

while the leaflet remains draped over the bar, elevating the bar at least until the leaflet stops blocking the beam;

identifying an elevation, of the bar from the beam, at which the leaflet stopped blocking the beam; and responsively to the identified elevation, assigning a flexibility value to the leaflet.

In an application, elevating the bar at least until the leaflet stops blocking the beam includes moving the bar through the beam.

In an application, the bar is movably coupled to a post via a linear actuator, and elevating the bar includes actuating the linear actuator.

In an application, the light source is a laser, and the beam of light is a laser beam, and:

positioning the bar such that the leaflet blocks the beam of light includes positioning the bar such that the leaflet blocks the laser beam; and elevating the bar at least until the leaflet stops blocking the beam includes elevating the bar at least until the leaflet stops blocking the laser beam.

In an application, the method further includes clamping the leaflet to the bar.

In an application, determining the flexibility of the leaflet includes determining the flexibility of a first leaflet, and the method further includes:

determining a flexibility of a second prosthetic heart valve leaflet;

identifying that the flexibility of the first leaflet and the flexibility of the second leaflet are within a threshold flexibility difference of each other; and in response to the identifying, assembling a prosthetic heart valve by attaching the first leaflet and the second leaflet to a frame.

In an application:
  positioning the bar such that the leaflet blocks the beam includes positioning the bar such that the leaflet blocks the beam from reaching a detector configured to detect the beam,
  elevating the bar at least until the leaflet stops blocking the beam includes elevating the bar at least until the detector detects the beam, and
  identifying the elevation includes identifying the elevation, from the beam, at which the bar was disposed when the detector detected the beam.

In an application, placing the leaflet across the bar includes placing the leaflet on a surface of a platform.

In an application, elevating the bar at least until the leaflet stops blocking the beam includes elevating the bar at least until a gap forms between the leaflet and the platform, and the beam passes through the gap.

In an application, the method further includes, prior to elevating the bar, adjusting a distance between the beam and the surface by adjusting a position of the light source with respect to the platform.

In an application, placing the leaflet on the surface of the platform includes placing the leaflet on the surface of the platform while the bar is disposed below the surface of the platform.

In an application, placing the leaflet across the bar includes placing the leaflet across the bar in a first orientation of the leaflet with respect to the bar, the elevation is a first elevation, and assigning the flexibility value to the leaflet includes assigning a first flexibility value to the leaflet, and the method further includes:

placing the leaflet across the bar in a second orientation of the leaflet with respect to the bar, and positioning the bar such that the leaflet drapes over the bar in the second orientation and blocks the beam;

while the leaflet remains draped over the bar in the second orientation, elevating the bar at least until the leaflet stops blocking the beam;

identifying a second elevation, of the bar from the beam, at which the leaflet in the second orientation stopped blocking the beam; and responsively to the identified second elevation, assigning a second flexibility value to the leaflet.

In an application, in the first orientation, the leaflet is draped symmetrically over the bar, and in the second orientation, the leaflet is draped asymmetrically over the bar.

In an application, placing the leaflet across the bar in the first orientation includes placing the leaflet within a first guide defined by a surface of a platform, and placing the leaflet across the bar in the second orientation includes placing the leaflet within a second guide defined by the surface of the platform.

In an application:

placing the leaflet across the bar in the first orientation includes placing the leaflet within the first guide while the first guide is aligned with the bar;

placing the leaflet across the bar in the second orientation includes placing the leaflet within the second guide while the second guide is aligned with the bar; and the method further includes, prior to placing the leaflet across the bar in the second orientation, aligning the second guide with the bar by rotating the platform with respect to the bar.

There is further provided, in accordance with an application of the present invention, apparatus for testing a prosthetic heart valve leaflet, the apparatus including:

a platform having a surface;

a bar:
movably coupled to the platform,
having an initial position with respect to the platform, in which the leaflet is placeable across the bar and in contact with the surface, and
being movable out of the initial position and away from the surface, so as to lift the leaflet away from the surface;

a gauge, coupled to the platform and the bar, and configured to measure an elevation between the bar and the platform; and a sensor, configured to detect a gap between the leaflet and the surface, and to generate a detection-signal indicative of detection of the gap.

In an application, the detection-signal is an audio signal, and the sensor is configured to generate the audio signal.

In an application, the detection-signal is a visual signal, and the sensor is configured to generate the visual signal.

In an application, the gauge is configured to measure an elevation-difference between (i) a present elevation between the bar and the platform, and (ii) an initial-position elevation between the bar and the platform when the bar is in the initial position.

In an application, the platform is shaped such that the surface is a horizontal surface, the bar is a horizontal bar, the apparatus further includes a vertical post that is coupled to and extends upward from the platform, and the bar is movably coupled to the platform by being coupled to the post and vertically slidable along the post.

In an application, the sensor:
includes at least one electrode positioned on the platform to be in contact with the leaflet,
is configured to detect electrical contact between the leaflet and the electrode, and
is configured to detect the gap by detecting a reduction in the electrical contact.

In an application, the apparatus further includes a controller, and:
the controller includes:
a display; and
circuitry that interfaces with the display, the gauge and the sensor, and
the circuitry, upon receipt of the detection-signal, drives the display to display the elevation.

In an application, the circuitry drives the gauge to measure the elevation upon receipt of the detection-signal.

In an application, the gauge is configured to generate an elevation-signal indicative of the measured elevation, and the apparatus further includes a controller, the controller including circuitry configured to:
receive the detection-signal and the elevation-signal, and
responsively to the detection-signal and the elevation-signal, to provide an output indicative of an elevation, between the bar and the platform, at which the gap is detected.

In an application, the circuitry is configured to, in response to the detection-signal, drive the gauge to generate the elevation-signal.

In an application, the gauge is configured to generate the elevation-signal independently of the circuitry receiving the detection-signal.

In an application, the apparatus further includes a display, and:
the circuitry is configured to drive the display to display the elevation independently of the circuitry receiving the detection-signal, and
the circuitry is configured to provide the output by maintaining, on the display, the elevation that was measured at a time that the detection-signal was received by the circuitry.

In an application, the sensor includes:
a laser, configured to emit a laser beam, and positioned to direct the laser beam to pass across the surface; and
a detector, configured to detect that the laser beam has passed across the surface.

In an application, the laser is positioned to direct the laser beam to pass across the surface within 2 mm of the surface.

In an application, the laser is positioned to direct the laser beam to pass across the surface between 0.4 and 0.6 mm of the surface.

In an application:
the platform is shaped such that the surface is a horizontal surface,
the bar is a horizontal bar,
the laser is positioned to direct the laser beam horizontally,
the apparatus further includes a vertical post that is coupled to and extends upward from the platform, and
the bar is movably coupled to the platform by being coupled to the post and vertically slidable along the post.

In an application, sliding of the bar vertically along the post moves the bar through the laser beam.

In an application, the laser beam is orthogonal to the bar.

In an application, the platform defines a guide that indicates an orientation in which the leaflet is to be placed on the surface.

In an application, the leaflet has a size and a shape, and the guide has a size and a shape that match the size and the shape of the leaflet.

In an application, the guide is a marking on the surface.

In an application, the guide is a depression in the surface.

In an application, the guide is a first guide, the orientation is a first orientation, and the platform further defines a second guide that indicates a second orientation that is different to the first orientation.

In an application, the platform is movable between a first-guide state and a second-guide state, such that:

in the first-guide state, the first guide is at a location with respect to the sensor, and is in the first orientation, and in the second-guide state, the second guide is at the location in the second orientation.

In an application, the second orientation is orthogonal to the first orientation.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

BRIEF DESCRIPTION OF THE DRAWINGS

FIGS. 1, 2A-E, and 3 are schematic illustrations of a system for testing prosthetic heart valve leaflets, in accordance with some applications of the invention.

DETAILED DESCRIPTION OF EMBODIMENTS

Figure 1:
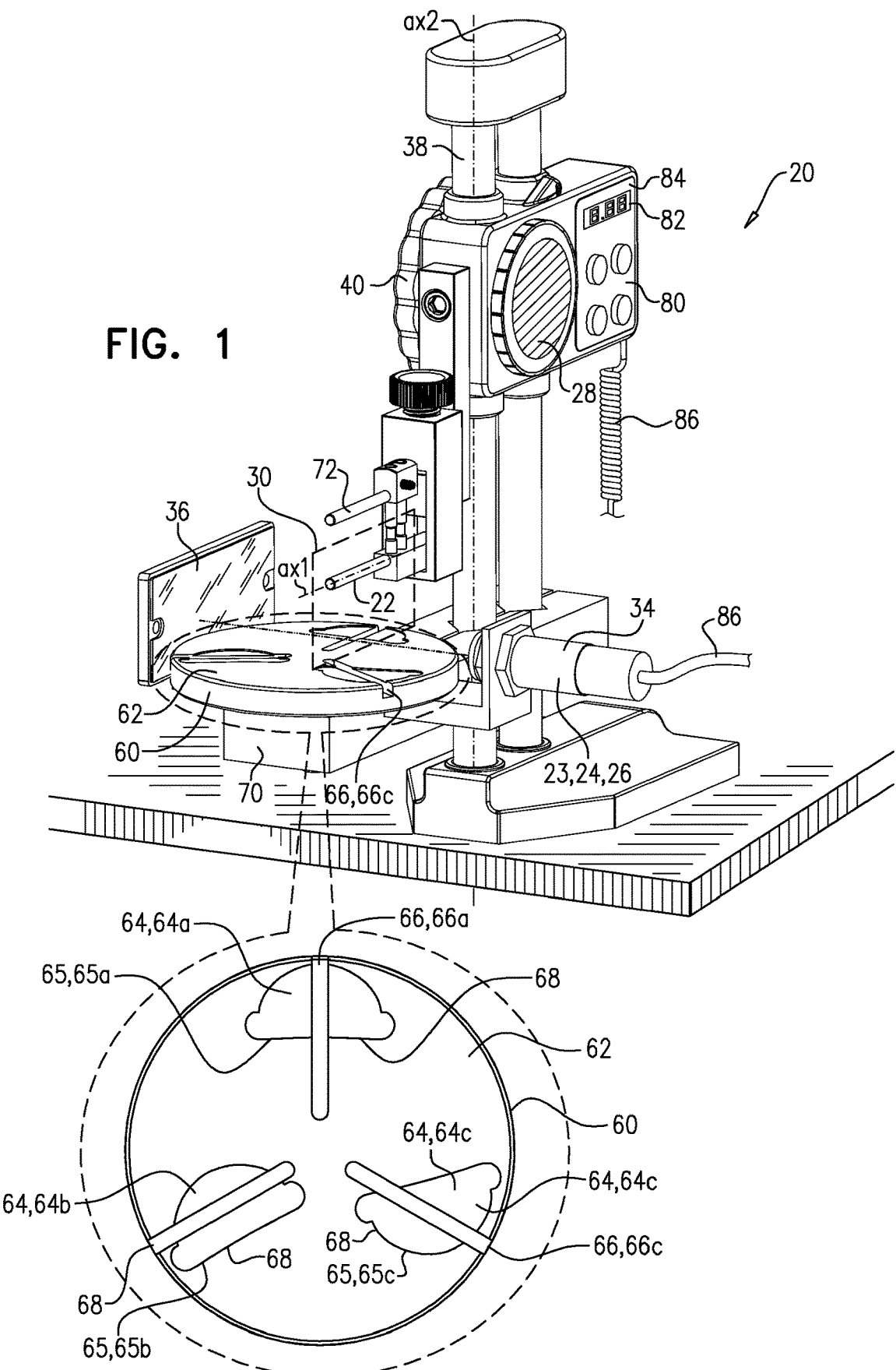

Reference is made to FIGS. 1, 2A-E, and 3, which are schematic illustrations of a system 20 for testing a prosthetic heart valve leaflet 10, in accordance with some applications of the invention. FIG. 1 shows system 20 alone, and FIGS. 2A-E show the system being used to test leaflet 10, in accordance with some applications of the invention. Prosthetic heart valve leaflets 10 are typically cut from animal tissue such as bovine pericardium, whose flexibility naturally varies between animals, and even between regions of the tissue within the same animal. Typically, system 20 is used to determine the flexibility of leaflets 10. For example, the system may be used to determine one or more flexibility values of the leaflet. The leaflet may be categorized according to the one or more flexibility values. Such categorization is hypothesized by the inventors to facilitate construction of prosthetic valves comprising such leaflets in order to reduce or eliminate regurgitation of blood between the prosthetic leaflets of the prosthetic valve. For example, for an individual prosthetic valve, prosthetic leaflets would be selected having similar or otherwise complementary flexibility values to one other.

System 20 comprises a horizontal bar 22, a sensor 23, and a gauge 28. Sensor 23 typically comprises a light source 24 and a detector 26. Bar 22 has a bar-axis ax1 that lies on a bar-plane 30. Bar 22 is movable with respect to light source 24, and bar-plane 30 is defined by the movement of axis ax1 when bar 22 is moved, as described hereinbelow. Typically, bar 22 is movable vertically, so bar-plane 30 is typically a vertical plane, as shown. Bar 22 is configured to support, along bar-axis ax1, the leaflet being tested such that the leaflet drapes over the bar. This draping is visible in FIGS. 2D-E.

Light source 24 is configured to emit a beam 32 of light, and is oriented to direct the beam through bar-plane 30. It is to be noted that, in this context, the term "light" (including in the specification and the claims) includes frequencies that are invisible to the human eye, but that are blocked by leaflet 10. Typically, light source 24 is a laser, configured to emit a laser beam.

Detector 26 is configured and positioned to detect beam 32, and is configured to generate a detection-signal indicative of detection of the beam. For example, detector 26 may be directly opposite light source 24, facing the light source. Alternatively, and as shown, system 20 may comprise a reflector 36 that reflects beam 32 toward detector 26, e.g., to facilitate more convenient positioning of detector 26. For some applications, and as shown, light source 24 and detector 26 are integrated within a housing 34, and reflector 36 reflects beam 32 back toward the housing from which the beam originated.

Gauge 28 is configured to measure a distance between bar 22 and beam 32 (e.g., an elevation of bar 22 above beam 32). It is to be noted that in this patent application, including in the specification and the claims, this includes measuring a distance that is indicative of the elevation of the bar above the beam, e.g., without directly measuring the specific distance between the bar and the beam. For example, if there is a fixed distance between beam 32 and another element of system 20, gauge 28 may measure the distance between bar 22 and the other element.

Bar 22 is movable with respect to light source 24 and beam 32, the movement of the bar defining bar-plane 30. Typically, this is achieved by bar 22 being movably coupled to a post (e.g., a vertical post) 38, to which light source 24 is coupled (e.g., fixedly coupled). For some applications, this is achieved by bar 22 being coupled to post 38 via a linear actuator 40, actuation of which moves the bar with respect to the post and within bar-plane 30. Actuator 40 may be mechanical, electronic, or any suitable type. Post 38 has a longitudinal axis ax2.

There is therefore provided, in accordance with some applications of the invention, apparatus for testing a prosthetic heart valve leaflet, the apparatus comprising:

a vertical post, having a longitudinal axis;

a horizontal bar having a bar-axis that lies on a vertical bar-plane, the bar being configured to support the leaflet along the bar-axis such that the leaflet drapes over the bar;

a linear actuator, movably coupling the bar to the post, actuation of the actuator moving the bar vertically in the bar-plane;

a light source, configured to emit a beam of light, and oriented to direct the beam through the bar-plane;

a gauge, configured to measure an elevation of the bar above the beam; and a detector, configured and positioned to detect the beam, and to generate a detection-signal indicative of detection of the beam.

For some applications, and as shown, bar 22 extends laterally away from post 38 (e.g., such that the post lies on bar-plane 30). For some applications, and as shown, light source 24 is disposed laterally from post 38. Typically, light source 24 is oriented to direct beam 32 through the bar-plane horizontally (e.g., such that the beam is perpendicular to the bar-plane). For some applications, the movement of bar 22 in the bar-plane, described hereinabove, includes movement of the bar through (e.g., vertically through) beam 32. That is, for some applications, bar 22 is coupled to post 38 such that the bar is movable, within the bar-plane, through (e.g., vertically through) the beam. It is to be noted that, in practice, leaflet 10 may block beam 32 from reaching bar 22 as the bar moves through the beam.

Figure 2A:
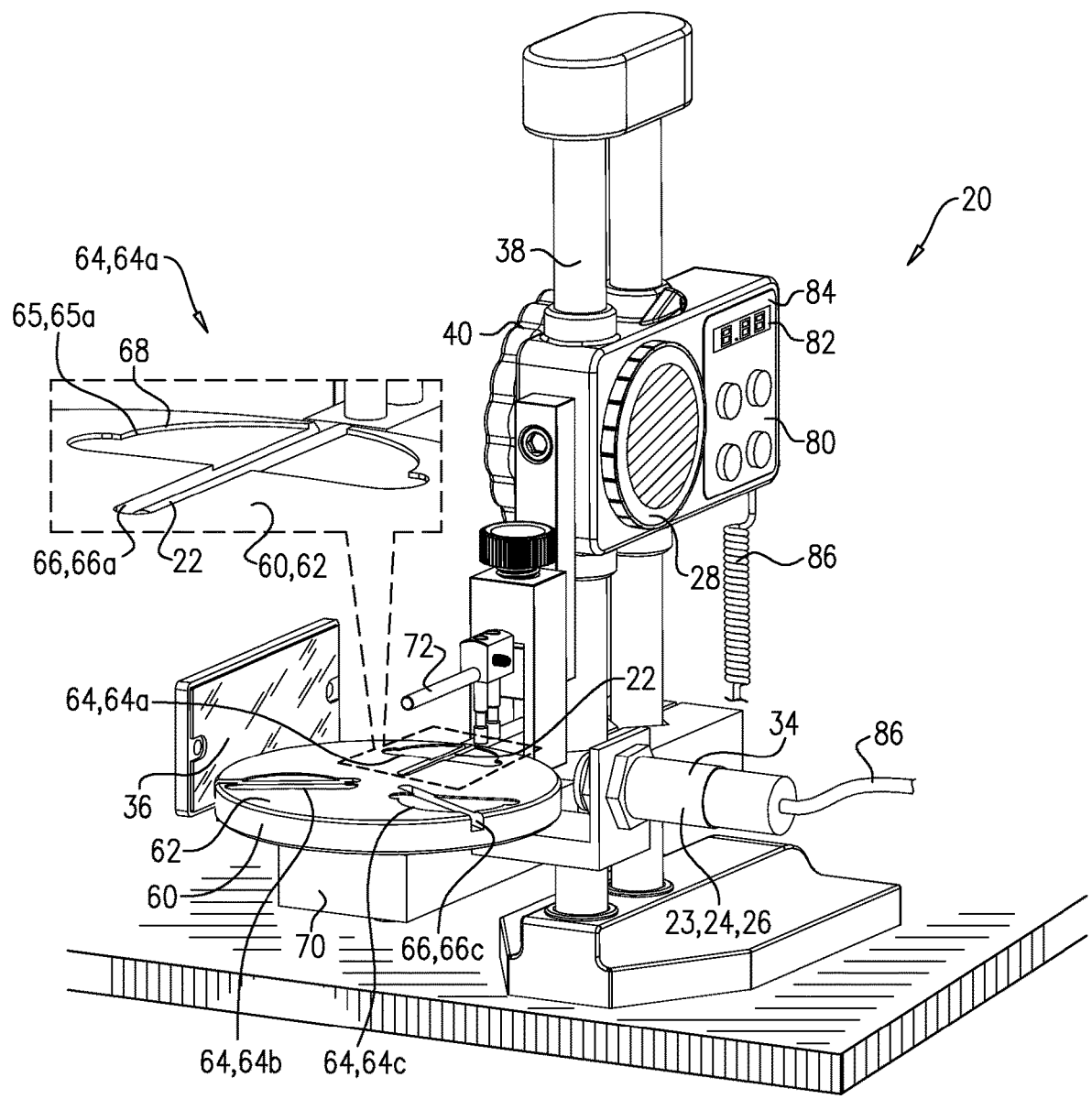
Figure 2C:
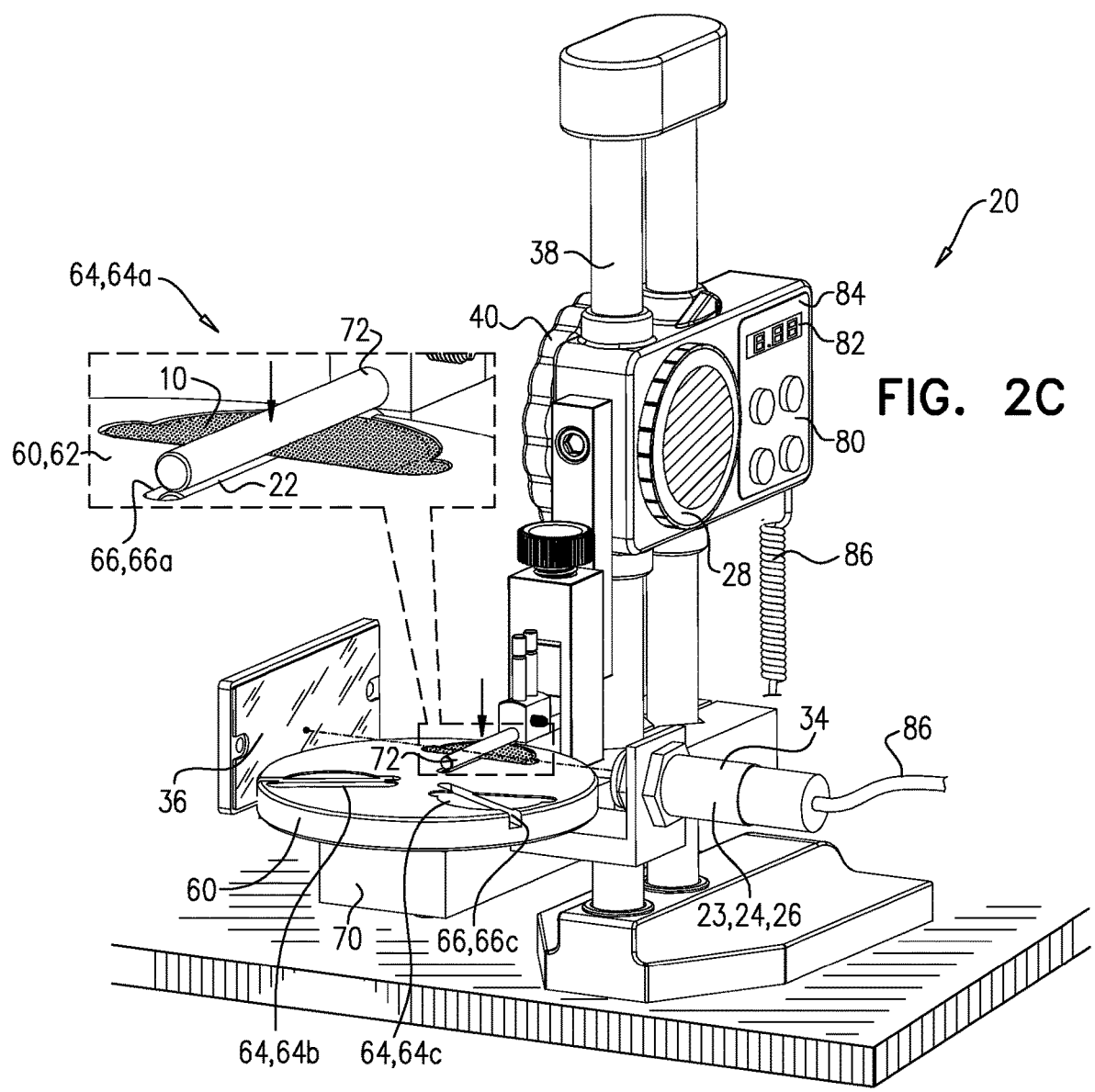
Figure 2D:
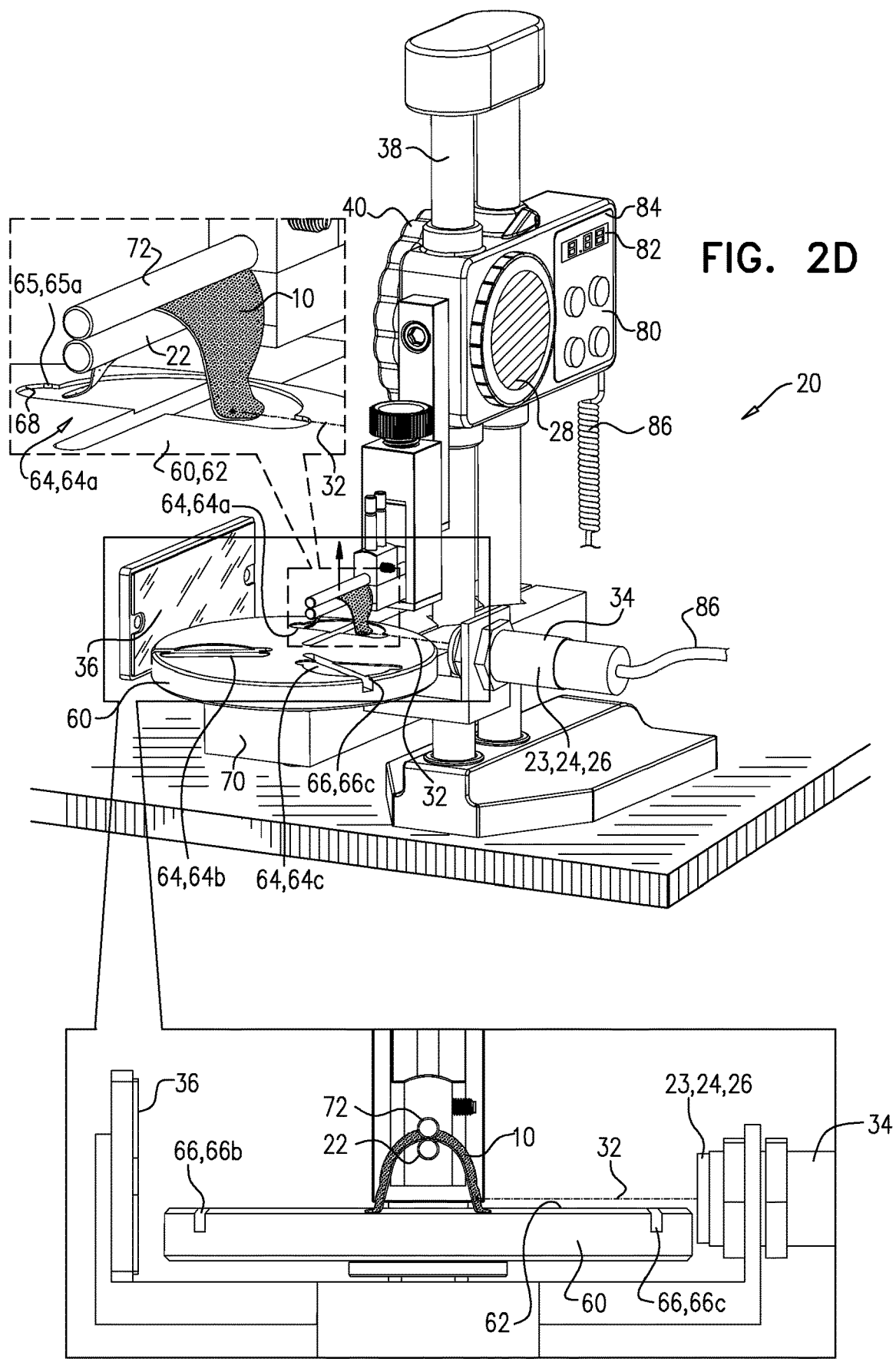
Figure 2E:
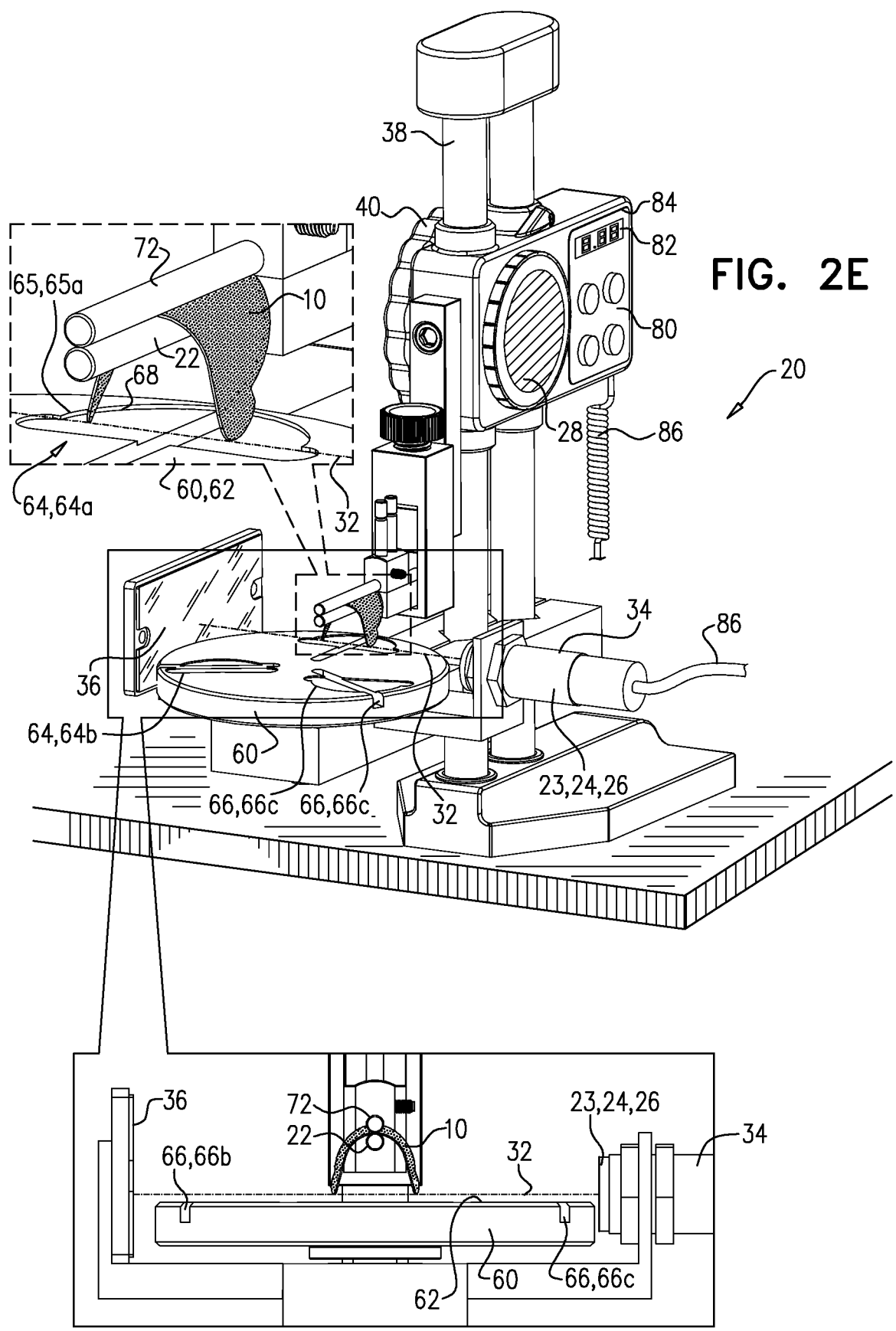

A brief, general description of a use of system 20 is as follows: Leaflet 10 is placed across bar 22, and the bar is positioned such that the leaflet drapes over the bar and blocks beam 32 (FIGS. 2B-D). While leaflet 10 remains draped over bar 22, the bar is elevated at least until the leaflet stops blocking the beam (FIG. 2E). An elevation of the bar from the beam at which the leaflet stopped blocking the beam is identified, and responsively to the identified elevation, a flexibility value is assigned to the leaflet. It is hypothesized by the inventors that, a leaflet which is more flexible about the bar-plane will drape more steeply, and therefore further down, from bar 22, thereby requiring a higher elevation above beam 32 before the leaflet stops blocking the beam.

For some applications, and as shown, system 20 comprises a platform 60 that has a surface 62 (e.g., an upper surface that is typically horizontal). Bar-plane 30 intersects platform 60, and the movement of bar 22 (e.g., via actuation of actuator 40) is with respect to the platform. Bar 22 has an initial position in which leaflet 10 is placeable across the bar and in contact with the surface. For some applications, in the initial position, bar 22 is disposed at least partly (e.g., completely) below the surface, as shown in FIG. 2A.

Typically, leaflets 10 that are to be tested using system 20 are cut from an animal tissue such as bovine pericardium. Further typically, leaflets 10 are cut to have consistent shape and size, the shape and size defining a leaflet-outline. For some applications, platform 60 has a guide 64 that defines a guide-outline 65 that corresponds to the leaflet-outline. Guide-outline 65 has a guide-outline position and a guide-outline orientation that indicate the position and orientation in which leaflet 10 is to be placed across the bar and in contact with the surface. Bar-plane 30 bisects guide-outline 65.

For some applications, system 20 has a plurality of guides 64, e.g., comprising a first guide 64a, a second guide 64b, and a third guide 64c, each of the guides at a defining a respective guide-outline 65a, 65b, and 65c. System 20 has a respective guide-state in which bar-plane 30 bisects a respective guide 64 (e.g., the guide-outline 65 thereof). For example, system 20 may have a first guide-state in which bar-plane 30 bisects guide 64a, a second guide-state in which the bar-plane bisects guide 64b, and a third guide-state in which the bar-plane bisects guide 64c. In its respective guide-state, each guide 64 is bisected by bar-plane 30 at a different angle. Typically, bar-plane 30 bisects at least one of the guides symmetrically when system 20 is in the corresponding guide-state, and bisects at least one of the other guides asymmetrically when the system is in the guide-state that corresponds to that guide.

Figure 3:
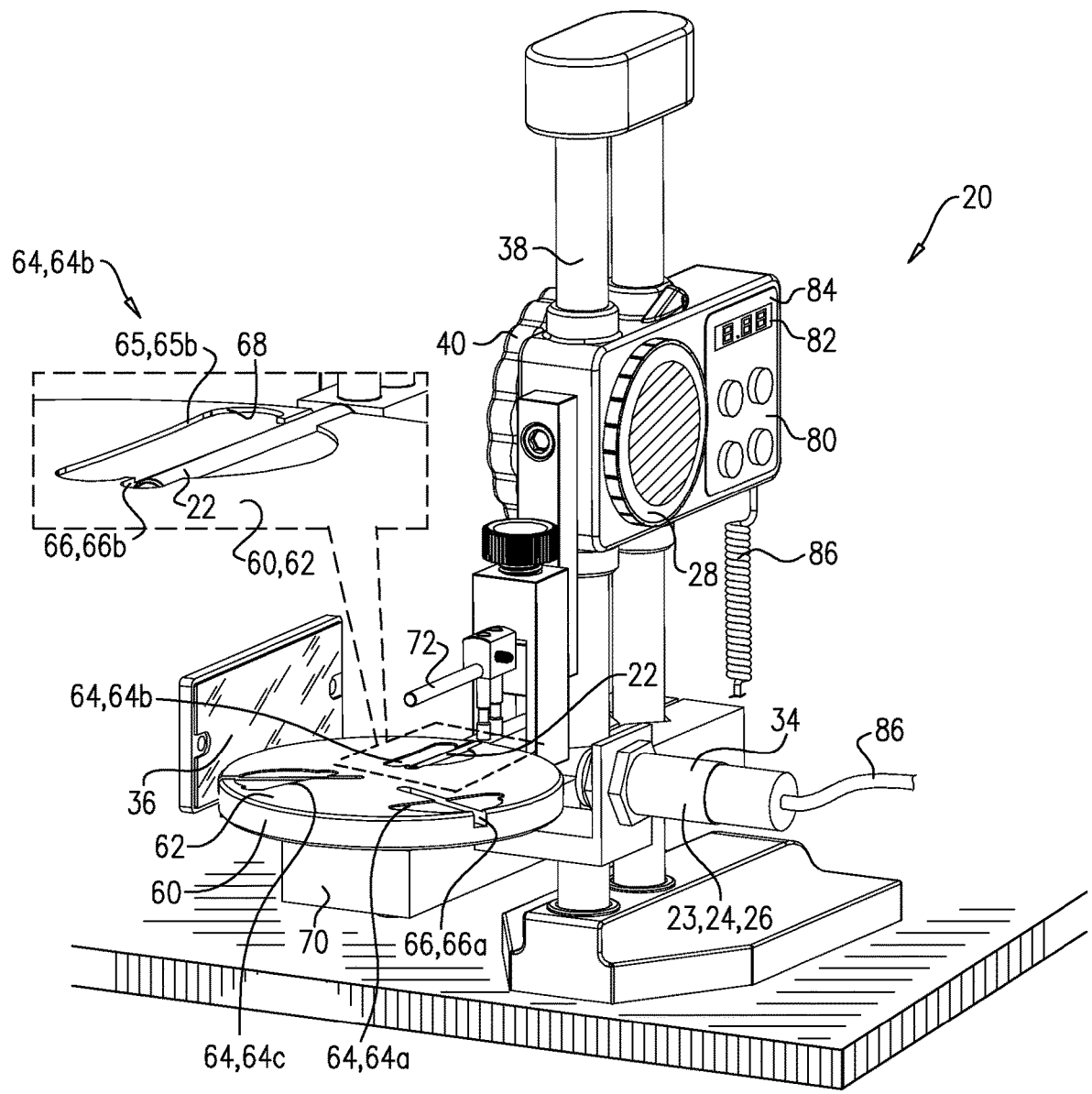

For some such applications, and as shown, platform 60 defines the plurality of guides 64, and is movably (e.g., rotatably) coupled to post 38 via a coupling 70. System 20 is transitioned between its guide-states via movement (e.g., rotation) of platform 60, the movement bringing the respective guides 64 into alignment with bar-plane 30. FIG. 2A shows system 20 in a first guide-state, in which bar-plane 30 bisects first guide 64a (e.g., first guide-outline 65a) symmetrically. FIG. 3 shows system 20 in a second guide-state, following rotation of platform 60, in which bar-plane 30 bisects the second guide 64b (e.g., second guide-outline 65b) asymmetrically.

Alternatively, system 20 comprises more than one platform 60, each platform defining a respective guide, and being removably couplable to a coupling (e.g., couplable to post 38 via the coupling). For such applications, each guide-state is achieved by coupling the corresponding platform to the coupling.

As described hereinabove, for some applications, in the initial position, bar 22 is disposed at least partly (e.g., completely) below the surface. To achieve this, platform 60 typically defines a longitudinal hollow 66 that lies on bar-plane 30. When bar 22 is in its initial position, it is disposed in hollow 66. Hollow 66 is shown as a groove in platform 60, but may alternatively be a slot cut all the way through the platform. Irrespective of whether platform 60 defines hollow 66, the initial position of bar 22 may be such that the placement of leaflet 10 across the bar places the leaflet in contact with the bar. Alternatively, the initial position of bar 22 (facilitated by the depth of hollow 66) may be such that the leaflet spans the hollow but does not actually touch the bar. In this context, the leaflet being "placed across the bar" includes such a configuration.

For applications in which system 20 has more than one guide 64 (e.g., applications in which platform 60 defines more than one guide), each guide typically has a corresponding hollow 66 appropriately aligned with the corresponding guide-outline 65. For example, and as shown, platform 60 may define a hollow 66a, a hollow 66b, and a hollow 66c. Transitioning of the system into a given guide-state aligns the corresponding hollow 66 with bar-plane 30.

For some applications, and as shown, each guide-outline 65 is defined by a ridge 68 that facilitates correct placement of leaflet 10, e.g., by at least partially inhibiting movement of the leaflet. For some such applications, and as shown, platform 60 defines each guide 64 as a depression, ridge 68 being the boundary of the depression. Alternatively, guide-outline 65 may simply be a marking.

For some applications, light source 24 is adjustably coupled to platform 60, such that a distance between the beam of light and the surface is adjustable by adjusting a position of the light source with respect to the platform. For some applications, light source 24 is positioned (or is positionable via adjustment) such that beam 32 passes across surface 62 within 2 mm of the surface, e.g., 0.1-1.5 mm (such as 0.1-1 mm, e.g., 0.1-0.5 mm, or such as 0.4-1.5 mm, e.g., 0.4-1 mm, such as 0.4-0.6 mm, such as about 0.46 mm) from the surface. For some applications, light source 24 is positioned such that beam 32 in effect skims surface 62. For such applications, system 20 is therefore configured to detect a gap between leaflet 10 and surface 62, and is used to determine the distance (e.g., elevation) between bar 22 and platform 60 at which the gap is formed. For such applications, there is therefore provided apparatus comprising:

a platform having a surface;
a bar:
   movably coupled to the platform,
   having an initial position with respect to the platform, in which the leaflet is placeable across the bar and in contact with the surface, and
   being movable out of the initial position and away from the surface, so as to lift the leaflet away from the surface;
a gauge, coupled to the platform and the bar, and configured to measure a distance between the bar and the platform; and
a sensor, configured to detect a gap between the leaflet and the surface, and to generate a detection-signal indicative of detection of the gap.

For some applications, detection of the gap is achieved through means other than detecting the unblocking of a beam of light. For example, instead of light source 24 and detector 26, sensor 23 may comprise at least one electrode positioned on platform 60 such that the electrode is in contact with leaflet 10 when the leaflet is placed across the bar and in contact with the platform. Via the electrode, the sensor detects electrical contact between the leaflet and the electrode, and detects the gap by detecting a reduction in (e.g., loss of) the electrical contact.

FIG. 2A shows system 20, in a first guide-state, with bar 22 in its initial position. Bar 22 is disposed in hollow 66, and is completely below surface 62 of platform 60. Leaflet 10 is positioned within guide-outline 65$a$ of guide 64$a$, thereby placing the leaflet across bar 22 (FIG. 2B).

For some applications, and as shown, system 20 further comprises a clamping element 72, movably coupled to bar 22, and configured to clamp leaflet 10 to the bar. FIG. 2C shows a step in which clamping element is moved toward the bar in order to clamp the leaflet to the bar, to prevent the leaflet from slipping off the bar when the bar is elevated. As shown, the clamping element may comprise a rod, parallel to the bar, and configured to clamp the leaflet against the bar along bar-axis ax1. For some applications, system 20 comprises a spring that provides a clamping force to element 72, the clamping force having a magnitude sufficiently great to secure leaflet 10, but sufficiently small to avoid damaging the leaflet.

Bar 22 is positioned such that leaflet 10 drapes over the bar and blocks beam 32. For some applications, in the initial position of bar 22, the bar is positioned in this manner. Alternatively, and as shown in FIG. 2D, bar 22 is positioned in this manner by elevating the bar.

While leaflet 10 remains draped over bar 22, the bar is elevated at least until the leaflet stops blocking beam 32 (FIG. 2E). Detector 26 detects beam 32, and responsively generates a detection-signal, indicative of detection of the beam. For some applications, the detection-signal is an audio signal. For some applications, the detection signal is a visual signal.

For some applications, the operator stops elevating bar 22 (e.g., actuating actuator 40) upon perceiving the detection-signal, reads the elevation measured by gauge 28, and responsively assigns a flexibility value to the leaflet.

For some applications, system 20 is at least partly automated, e.g., by electronically coupling sensor 23 to gauge 28. This is represented by a cable 86 connecting housing 34 to controller 80, but it is to be understood that the scope of the invention includes other means, both wired and wireless, of electronically coupling the sensor to the controller. For example, system 20 may comprise a controller 80 that comprises a display 82, and circuitry 84 that interfaces with the display, gauge 28, and sensor 23 (e.g., detector 26 thereof). Controller 80 (e.g., circuitry 84) is configured to receive the detection-signal, and to responsively drive display 82 to display the elevation of bar 22, with respect to beam 32, at which the beam was detected.

For example, gauge 28 may continuously (or repeatedly) measure the elevation of bar 22 with respect to beam 32, e.g., continuously providing an elevation-signal. Upon receipt of the detection-signal, controller 80 (e.g., circuitry 84) drives display 82 to display the elevation at which the beam was detected (i.e., the elevation measured at the time that the detection-signal was received by the controller), and continues to display that elevation even if bar 22 is moved further. Alternatively, gauge 28 may only measure the elevation in response to the detection-signal (e.g., controller 80 may be configured to, in response to receiving the detection-signal, drive gauge 28 to measure the elevation).

There is therefore provided, in accordance with some applications of the invention, apparatus comprising:
- a bar having a bar-axis, the bar being configured to support a prosthetic heart valve leaflet along the bar-axis such that the leaflet drapes over the bar;
- a light source, configured to emit a beam of light;
- a detector, configured to detect the beam, and to generate a detection-signal indicative of detection of the beam;
- a linear actuator, movably coupling the bar to the light source, actuation of the actuator moving the bar with respect to the beam;
- a gauge, configured to measure an elevation of the bar above the beam, the elevation changing with the moving of the bar by the actuator;
- a display, and
- circuitry, electrically connected to the detector, the gauge, and the display, and configured:
  - to receive, from the gauge, the measured elevation,
  - to receive the detection-signal from the detector, and
  - in response to the detection-signal, to drive the display to display the elevation that was measured when the detection-signal was received by the circuitry.

It is to be understood that display 82 is merely an example of an output that controller 80 (e.g., circuitry 84 thereof) may provide in response to receipt of the detection-signal, and that the scope of the invention includes the controller providing other outputs, such as an electronic output signal that is received by a computer system.

As described hereinabove, the flexibility of animal tissue from which leaflets 10 are typically cut is naturally variable. Moreover, such tissue may have anisotropic flexibility, and therefore each leaflet 10 may be more flexible on one axis than on another. It is hypothesized by the inventors that testing the flexibility of leaflets on more than one axis advantageously improves matching of complementary leaflets for use within a single prosthetic valve. Therefore, as described hereinabove, for some applications system 20 has a plurality of guides 64 and a plurality of guide-states, for testing the flexibility of leaflet 10 in different orientations (e.g., rotational orientations) with respect to bar 22. In the example shown, system 20 has three guides 64 and three guide-states. FIG. 3 shows system 20 after it has been transitioned into another guide-state by rotating platform 60 such that guide 64$b$ is aligned with (and bisected by) bar-plane 30. The steps described with reference to FIGS. 2B-E are typically repeated for each guide state. When in its corresponding guide-state, guide 64$b$ is disposed with respect to bar-plane 30 at an orientation that is orthogonal to that of guide 64$a$ in its corresponding guide-state. When in its corresponding guide-state, guide 64$c$ is disposed with respect to bar-plane 30 at an orientation that is between that of guide 64$a$ in its corresponding guide-state, and that of guide 64$b$ in its corresponding guide state.

For some applications, for one or more of the guide states, leaflet 10 is tested one side up and the other side up.

For some applications, system 20 does not comprise post 38, and another mechanism is used to movably couple bar 22 to light source 24.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for determining a flexibility of a prosthetic heart valve leaflet, the method comprising:
    placing the leaflet across a bar, and positioning the bar such that the leaflet drapes over the bar and blocks a beam of light emitted by a light source;
    while the leaflet remains draped over the bar, elevating the bar at least until the leaflet stops blocking the beam; and
    identifying an elevation, of the bar from the beam, at which the leaflet stopped blocking the beam.

2. The method according to claim 1, wherein elevating the bar at least until the leaflet stops blocking the beam comprises moving the bar through the beam.

3. The method according to claim 1, wherein the bar is movably coupled to a post via a linear actuator, and wherein elevating the bar comprises actuating the linear actuator.

4. The method according to claim 1, wherein the light source is a laser, and the beam of light is a laser beam, and wherein:
    positioning the bar such that the leaflet blocks the beam of light comprises positioning the bar such that the leaflet blocks the laser beam; and
    elevating the bar at least until the leaflet stops blocking the beam comprises elevating the bar at least until the leaflet stops blocking the laser beam.

5. The method according to claim 1, further comprising clamping the leaflet to the bar.

6. The method according to claim 1, wherein determining the flexibility of the leaflet comprises determining the flexibility of a first leaflet, and wherein the method further comprises:
    determining a flexibility of a second prosthetic heart valve leaflet;
    identifying that the flexibility of the first leaflet and the flexibility of the second leaflet are within a threshold flexibility difference of each other; and
    in response to the identifying, assembling a prosthetic heart valve by attaching the first leaflet and the second leaflet to a frame.

7. The method according to claim 1, wherein:
    positioning the bar such that the leaflet blocks the beam comprises positioning the bar such that the leaflet blocks the beam from reaching a detector configured to detect the beam,
    elevating the bar at least until the leaflet stops blocking the beam comprises elevating the bar at least until the detector detects the beam, and
    identifying the elevation comprises identifying the elevation, from the beam, at which the bar was disposed when the detector detected the beam.

8. The method according to claim 1, wherein placing the leaflet across the bar comprises placing the leaflet on a surface of a platform.

9. The method according to claim 8, wherein elevating the bar at least until the leaflet stops blocking the beam comprises elevating the bar at least until a gap forms between the leaflet and the platform, and the beam passes through the gap.

10. The method according to claim 9, further comprising, prior to elevating the bar, adjusting a distance between the beam and the surface by adjusting a position of the light source with respect to the platform.

11. The method according to claim 8, wherein placing the leaflet on the surface of the platform comprises placing the leaflet on the surface of the platform while the bar is disposed below the surface of the platform.

12. The method according to claim 1, wherein:
    placing the leaflet across the bar comprises placing the leaflet across the bar in a first orientation of the leaflet with respect to the bar,
    the elevation is a first elevation, and
    the method further comprises:
        placing the leaflet across the bar in a second orientation of the leaflet with respect to the bar, and positioning the bar such that the leaflet drapes over the bar in the second orientation and blocks the beam;
        while the leaflet remains draped over the bar in the second orientation, elevating the bar at least until the leaflet stops blocking the beam; and
        identifying a second elevation, of the bar from the beam, at which the leaflet in the second orientation stopped blocking the beam.

13. The method according to claim 12, wherein in the first orientation, the leaflet is draped symmetrically over the bar, and in the second orientation, the leaflet is draped asymmetrically over the bar.

14. The method according to claim 12, wherein placing the leaflet across the bar in the first orientation comprises placing the leaflet within a first guide defined by a surface of a platform, and wherein placing the leaflet across the bar in the second orientation comprises placing the leaflet within a second guide defined by the surface of the platform.

15. The method according to claim 14, wherein:
    placing the leaflet across the bar in the first orientation comprises placing the leaflet within the first guide while the first guide is aligned with the bar;
    placing the leaflet across the bar in the second orientation comprises placing the leaflet within the second guide while the second guide is aligned with the bar; and
    the method further comprises, prior to placing the leaflet across the bar in the second orientation, aligning the second guide with the bar by rotating the platform with respect to the bar.

16. The method according to claim 1, further comprising, responsively to the identified elevation, assigning a flexibility value to the leaflet.

* * * * *